US012807653B2

(12) United States Patent
Hu et al.

(10) Patent No.: US 12,807,653 B2
(45) Date of Patent: Nov. 24, 2026

(54) CLD PROTEIN MUTANT AND APPLICATION THEREOF

(71) Applicant: Chengdu Virogen Biopharmaceutical Co., LTD., Sichuan (CN)

(72) Inventors: Qinxue Hu, Sichuan (CN); Ming Fu, Sichuan (CN); Tao Du, Sichuan (CN)

(73) Assignee: Chengdu Virogen Biopharmaceutical Co., Ltd., Sichuan (CN)

( * ) Notice: Subject to any disclaimer, the term of this patent is extended or adjusted under 35 U.S.C. 154(b) by 900 days.

(21) Appl. No.: 17/931,395

(22) Filed: Sep. 12, 2022

(65) Prior Publication Data

US 2024/0059745 A1 Feb. 22, 2024

Related U.S. Application Data

(63) Continuation of application No. PCT/CN2022/113737, filed on Aug. 19, 2022.

(51) Int. Cl.
*C07K 14/16* (2006.01)
*A61K 38/00* (2006.01)

(52) U.S. Cl.
CPC ............ *C07K 14/162* (2013.01); *A61K 38/00* (2013.01)

(58) Field of Classification Search
None
See application file for complete search history.

(56) References Cited

FOREIGN PATENT DOCUMENTS

| | | |
|---|---|---|
| CN | 102617738 A | 8/2012 |
| CN | 103992396 A | 8/2014 |
| CN | 106701692 A | 5/2017 |
| CN | 107224578 A | 10/2017 |
| CN | 107973851 A | 5/2018 |
| CN | 110054668 A | 7/2019 |
| CN | 113563480 A | 10/2021 |
| WO | 2010008084 A1 | 1/2010 |
| WO | 2013040766 A1 | 3/2013 |

OTHER PUBLICATIONS

Chinese Office Action dated Mar. 2, 2022 for corresponding CN Application No. 202110786982.1.
Chinese Office Action dated Dec. 9, 2022 for corresponding CN Application No. 202110786982.1.
International Search Report dated Nov. 2, 2022 for corresponding PCT Application No. PCT/CN2022/113737.
Duan et al. "Chain A, gpl120" Dec. 1, 20220, PDB:6L1Y_A, retrieved from http://www/ncbi.nlm.nih.gov.
Fu et al. "Fusion Proteins CLD and CLDmut Demonstrate Potent and Broad Neutralizing Activity against HIV-1", Viruses, (2022) vol. 14, 1365.
NCBI Blast:Protein Sequence, Jan. 30, 2023, RID-XEZTYWC6016.

*Primary Examiner* — Peter Johansen
(74) *Attorney, Agent, or Firm* — Tarolli, Sundheim, Covell & Tummino LLP

(57) ABSTRACT

The present application relates to genetic engineering field, in particular to a CD4-Linker-DC-SIGN (CLD) protein mutant and application thereof. The CLD protein mutant is shown in SEQ ID NO. 4. The applicant mutates cysteine at position 60 of CD4 in the first generation CLD recombinant proteins into serine, and the obtained CLD protein mutant increases its ability to inhibit tested HIV-1 strains by 2-3 orders of magnitude. The neutralizing activity of the obtained CLD protein mutant against viruses is improved significantly, and such difference is more obvious in tested HIV-1T/F (transmitter/founder) viruses. The CLD protein mutant has greatly improved binding efficiency to HIV-1 virus. Furthermore, a complex formed by the CLD protein mutant or the recombinant CLD protein and an envelope protein can serve as an immunogen to highly induce antibodies targeting V1/V2 regions of the envelope protein, and shows wide application prospects.

8 Claims, No Drawings

Specification includes a Sequence Listing.

CLD PROTEIN MUTANT AND APPLICATION THEREOF

CROSS-REFERENCE TO RELATED APPLICATIONS

The present application is a Bypass Continuation of PCT Application Serial No. PCT/CN2022/113737, filed 19 Aug. 2022, which claims priority to Chinese Patent Application No. 202110786982.1, titled "A CLD PROTEIN MUTANT AND APPLICATION THEREOF" filed on Jul. 12, 2021, the contents of which are incorporated herein by reference in their entirety.

SEQUENCE LISTING

The instant application contains a Sequence Listing, which has been submitted electronically in TXT format and is hereby incorporated by reference in its entirety. Said TXT copy, created on 17, Sep. 2026, with the filename of "DF222443US_Sequence_listing_CN2021107869821.txt" and is 13,421 kilobytes in size.

TECHNICAL FIELD

The present application relates to the field of genetic engineering, in particular to a CD4-Linker-DC-SIGN (CLD) protein mutant and application thereof.

BACKGROUND

Human immunodeficiency viruses (HIV-1) are pathogens of acquired immunodeficiency syndrome (AIDS). Due to the high variability of the HIV-1 and the lack of understanding of human immunity mechanisms, effective HIV-1 vaccines have not been developed at present. Treatment of HIV-1 infected patients and prevention of HIV-1 infection mainly depend on anti-HIV drugs. However, as the HIV-1 is highly variable, long-term use of the anti-HIV drugs in clinic will necessarily lead to virus resistance and tolerance. It is urgent to develop a novel antiviral drug for maintaining the sustainability of HIV-1 treatment.

Types of target cells that can be infected by HIV-1 include T cells, macrophages and some types of DC cells, all of which have a common characteristic that CD4 molecules and coreceptor molecules are expressed on their surface. The HIV-1 can be divided into R5 viruses and X4 viruses depending on whether CCR5 coreceptors or CXCR4 coreceptors are involved in the infection process of cells by HIV-1. Some subtypes of AIDS viruses are also divided into an intermediate type of R5X4 viruses as both CCR5 and CXCR4 are involved in the infection process. The infection process of target cells by HIV-1 can be actually regarded as a process of viral envelope proteins recognizing and binding to CD4 and the coreceptors. However, all viruses, either the R5, the X4 or the R5X4, require the CD4 to complete the infection process. It is sufficient for cells to be infected by the virus by binding the HIV-1 envelope protein to the CD4 and the coreceptors. Therefore, a CD4-binding site on the HIV-1 envelope protein can serve as a target in preventing the HIV-1 from infecting the cells.

Dendritic cell-specific ICAM-grabbing non-integrin (DC-SIGN) is a lectin recognition protein expressed on the surface of DCs, which can enrich the viruses by binding to polysaccharides on the surface of the envelope protein, and soluble DC-SIGN can inhibit the binding of the HIV-1 envelope protein with the DCs.

Previously, the applicant tried to express the fusion of CD4 and DC-SIGN in prokaryotic cells (CN 102617738A), and the results showed that the designed recombinant protein CLD had higher antiviral activity; and its ability to neutralize virus reached a microgram level. However, the applicant found in later experiments that the recombinant protein CLD was less effective against most T/F strains.

In view of the above problems, the present application made some improvements on the recombinant fusion protein. Specifically, cysteine at position 60 of the CD4 domain of the recombinant fusion protein is mutated to serine, a histidine (HIS) sequence used in the prokaryotic expression is deleted; and the expression is conducted in a eukaryotic system. The obtained recombinant protein CLD mutant is greatly improved in activity than that of the first generation CLD expressed in the prokaryotic system and has a broad spectrum, and thus is very promising to become a next-generation anti-HIV-1 drug.

SUMMARY

One objective of the present application is to provide a CLD protein mutant, and the CLD protein mutant is shown in SEQ ID NO. 4.

Another objective of the present application is to provide a composition of CLD protein mutants.

Further objective of the present application is to provide a complex immunogen.

Yet another objective of the present application is to provide use of the CLD protein mutant or the composition thereof or the complex immunogen in the manufacture of an anti-HIV-1 drug.

The final objective of the present application is to provide use of the complex immunogen in the manufacture of an anti-HIV-1 drug.

In order to fulfill the above objectives, following technical solutions are adopted by the present application.

A CLD protein mutant, wherein the mutant is shown in SEQ ID NO. 4. Compared with the first generation CLD provided in CN 102617738A, the cysteine at position 60 of CD4 of the mutant is mutated to serine. Products encoded have greatly improved binding efficiency to HIV-1 virus, and can maintain the stability of the proteins.

A composition of CLD protein mutants, wherein the composition is a combination of SEQ ID NO. 4 and any one, two, three or four of the proteins as shown in SEQ ID NOs. 1, 2, 3, and 5. Use of the CLD protein mutant in the manufacture of an anti-HIV-1 drug, in which any one or any combination of the proteins as shown in SEQ ID NOs. 1 to 5 is served as the only main effective component or one of the main effective components for manufacturing the anti-HIV-1 drugs.

A complex immunogen consisting of a recombinant CLD protein and an HIV-1 envelope protein, includes any one of proteins as shown in the SEQ ID NO. 1 to SEQ ID NO. 5 and HIV-1 gp160, HIV-1 gp140 or HIV-1 gp120.

The present application further provides a complex immunogen consisting of a recombinant CLD protein and an HIV-1 envelope protein, in which the recombinant CLD protein is any one of proteins as shown in the SEQ ID NO. 6 to SEQ ID NO. 8.

Use of the complex immunogen in the manufacture of an anti-HIV-1 drug also falls within the protection scope of the present application.

Compared with the prior art, the present application has following advantages and achieves following effects:

Compared with prokaryotic recombinant CLD, the recombinant protein CLD mutant expressed in the eukaryotic system increases its ability to inhibit tested HIV-1 strains by 2-3 orders of magnitude and significantly improves its ability to neutralize viruses, and such difference is more obvious in the tested HIV-1 T/F (transmitter/founder) viruses. It can be seen the CLD mutant exhibits wide application prospects. Compared with the prokaryotically expressed CLD and eukaryotically expressed CLD non-mutant recombinant fusion proteins, the CLD mutant expressed in eukaryotic system is more stable in a solution, and has slight changes in the ability to inhibit the HIV-1. In an anti-HIV-1 infection experiment, the inhibiting activity of the eukaryotically expressed CLD mutant recombinant fusion protein against part of strains increased 3 to 5 times in comparison to the non-mutant.

The series of CLD mutant proteins obtained in the present application have a good inhibiting effect on HIV-1. The CLD mutant proteins in solution state can form a tetramer with a bifunctional structural domain, and after the DC-SIGN functional domain in the multimerized CLD mutant binds to the envelope protein, the local concentration of the tetramerized CD4 molecules binding with the CD4-binding site on the envelope protein is increased, and thus the neutralizing activity against the HIV-1 is improved.

Compared with HIV-1 envelope proteins mixed with CD4 or DC-SIGN or a single envelope protein, the complex consisting of the series of the CLD mutant proteins obtained in the present application and the HIV-1 envelope protein can induce more vigorous immune responses targeting gp120 V1V2 epitopes as immunogen, but the resulted immune responses targeting gp120 V3C3 epitopes are weaker.

DETAILED DESCRIPTION OF THE EMBODIMENTS

The technical solutions stated in the present application are all conventional solutions in the prior art unless otherwise specified; and reagents or materials are all available commercially unless otherwise specified.

Example 1

Construction of eukaryotic expression vectors pCDNA-C25NDC60S, pCDNA-C30NDC60S, pCDNA-C35NDC60S, pCDNA-C40NDC60S and pCDNA-C45NDC60S.

Primers used in this example are shown as follows:

```
P1-F:
                                        (SEQ ID NO: 9)
GAATTCCCTGCTGCTGCTCCTGCCTCAGGCCCAGGCTGTGAAGAAAGTG
GTGCTGGGCAAAAAAGGGGATACAGTGGAACTGACCTGTA;

P1-R:
                                       (SEQ ID NO: 10)
TTAAACGGGCCCTCTAGACTCGAGCTACGCAGGAGGGGGGTTTGGGGTG.

P2-F:
                                       (SEQ ID NO: 11)
ATGGACCGGGCCAAGCTGCTGCTCCTGCTCCTGCTGCTGCTCCTGCCTC
TGCAGATATCCAGCACAGTGG;

P2-R:
                                       (SEQ ID NO: 12)
GAGGCAGGAGCAGCAGCAGGAGCAGGAGCAGCAGCTTGGCCCGGTCCAT
GAATTCCACCACACTGGACTAGTGG.
```

-continued

```
P3-F:
                                       (SEQ ID NO: 13)
GATCGCGCTGACTCAAGAAGAAGCCTTTGGGAC;

P3-R:
                                       (SEQ ID NO: 14)
GTCCCAAAGGCTTCTTCTTGAGTCAGCGCGATC.
```

(1) Construction of the pCDNA-C25NDC60S:

Taking pET28a-C25D (CN 102617738A) as a template, PCR was conducted with primers P1-F and P1-R, and the obtained nucleic acid amplification products were subjected to electrophoresis before gel recovery. Taking pCDNA3.1 as a template, PCR was conducted with primers P2-F and P2-R, and the obtained nucleic acid amplification products were subjected to electrophoresis before gel recovery. Homologous recombination was conducted by using a homologous recombination kit from Vazyme. 15 μl of recombination system was added to 100 μl of *Escherichia coli* competent cells DH5 alpha, mixed uniformly, the obtained mixtures were transformed by heat shock at 42° C., and then 800 μl of LB culture solution was added thereto for oscillating culture at 37° C. for 1 hour. The obtained bacteria solution was coated on an LB culture medium with kanamycin resistance, and incubated for overnight at 37° C. 6 colonies were selected from the plate on which the transformation took place, and inoculated into 5 ml of kanamycin-containing LB for oscillating culture overnight at 37° C. Plasmids were then extracted by a plasmid extraction kit, sequenced and validated, and the successfully constructed plasmid was designated as pCDNA-C25ND.

With the properly constructed pCDNA-C25ND serving as a template and P3-F and P3-R serving as a primer pair, PCR amplification was conducted by using a Takara circular PCR kit. 2 μl of dpnI was added to every 50 μl of PCR system to digest at 37° C. for 2 hours. 15 μl of the obtained digestive solution was taken and added to 100 μl of *Escherichia coli* competent cells DH5 alpha, mixed uniformly, the obtained mixtures were transformed by heat shock at 42° C., and then 800 μl of LB culture solution was added thereto for oscillating culture at 37° C. for 1 hour. The obtained bacteria solution was coated on the LB culture medium with kanamycin resistance, and then incubated for overnight at 37° C. 6 colonies were selected from the plate on which the transformation took place, and inoculated into 5 ml of kanamycin-containing LB for oscillating culture overnight at 37° C. Plasmids were then extracted by the plasmid extraction kit, sequenced and validated, and the successfully constructed plasmid was designated as pCDNA-C25NDC60S. The pCDNA-C25NDC60S codes parts including the 178aa at the N-terminal of CD4 D1D2 domain, the NECK and CRD of the DC-SIGN, and a linker containing 25 amino acids. In the pCDNA-C25NDC60S, the cysteine at position 60 of CD4 was mutated to serine.

(2) Construction of the pCDNA-C30NDC60S:

Taking pET28a-C30D (CN 102617738A) as a template, PCR was conducted with primers P1-F and P1-R, and the obtained nucleic acid amplification products were subjected to electrophoresis before gel recovery. Taking pCDNA3.1 as a template, PCR was conducted with primers P2-F and P2-R, and the obtained nucleic acid amplification products were subjected to electrophoresis before gel recovery. Homologous recombination was conducted by using a homologous recombination kit from Vazyme. 15 μl of recombination system was added to 100 μl of *Escherichia coli* competent cells DH5 alpha, mixed uniformly, the obtained mixtures were transformed by heat shock at 42° C., and then 800 μl of LB culture solution was added thereto for oscillating culture at 37° C. for 1 hour. The obtained bacteria solution was coated on an LB culture medium with kanamycin resistance, and incubated for overnight at 37° C. 6 colonies were selected from the plate on which the transformation took place, and inoculated into 5 ml of kanamycin-containing LB for oscillating culture overnight at 37° C. Plasmids were then extracted by a plasmid extraction kit, sequenced and validated, and the successfully constructed plasmid was designated as pCDNA-C30ND.

With the properly constructed pCDNA-C30ND serving as a template and P3-F and P3-R serving as a primer pair, PCR amplification was conducted by using a Takara circular PCR kit. 2 μl of dpnI was added to every 50 μl of PCR system to digest at 37° C. for 2 hours. 15 μl of the obtained digestive solution was taken and added to 100 μl of *Escherichia coli* competent cells DH5 alpha, mixed uniformly, the obtained mixtures were transformed by heat shock at 42° C., and then 800 μl of LB culture solution was added thereto for oscillating culture at 37° C. for 1 hour. The obtained bacteria solution was coated on the LB culture medium with kanamycin resistance, and then incubated for overnight at 37° C. 6 colonies were selected from the plate on which the transformation took place, and inoculated into 5 ml of kanamycin-containing LB for oscillating culture overnight at 37° C. Plasmids were then extracted by the plasmid extraction kit, sequenced and validated, and the successfully constructed plasmid was designated as pCDNA-C30NDC60S. The pCDNA-C30NDC60S codes parts including the 178 aa at the N-terminal of CD4 D1D2 domain, the NECK and CRD of the DC-SIGN, and a linker containing 30 amino acids. In the pCDNA-C30NDC60S, the cysteine at position 60 of CD4 was mutated to serine.

(3) Construction of the pCDNA-C35NDC60S:

Taking pET28a-C35D (CN 102617738A) as a template, PCR was conducted with primers P1-F and P1-R, and the obtained nucleic acid amplification products were subjected to electrophoresis before gel recovery. Taking pCDNA3.1 as a template, PCR was conducted with primers P2-F and P2-R, and the obtained nucleic acid amplification products were subjected to electrophoresis before gel recovery. Homologous recombination was conducted by using a homologous recombination kit from Vazyme. 15 μl of recombination system was added to 100 μl of *Escherichia coli* competent cells DH5 alpha, mixed uniformly, the obtained mixtures were transformed by heat shock at 42° C., and then 800 μl of LB culture solution was added for oscillating culture at 37° C. for 1 hour. the obtained bacteria solution was coated on an LB culture medium with kanamycin resistance, and incubated for overnight at 37° C. 6 colonies were selected from the plate on which the transformation took place, and inoculated into 5 ml of kanamycin-containing LB for oscillating culture overnight at 37° C. Plasmids were then extracted by a plasmid extraction kit, sequenced and validated, and the successfully constructed plasmid was designated as pCDNA-C35ND.

With the properly constructed pCDNA-C35ND serving as a template and P3-F and P3-R serving as a primer pair, PCR amplification was conducted by using a Takara circular PCR kit. 2 μl of dpnI was added to every 50 μl of PCR system to digest at 37° C. for 2 hours. 15 μl of the obtained digestive solution was taken and added to 100 μl of *Escherichia coli* competent cells DH5 alpha, mixed uniformly, the obtained mixtures were transformed by heat shock at 42° C., and then 800 μl of LB culture solution was added for oscillating culture at 37° C. for 1 hour. The obtained bacteria solution was coated on the LB culture medium with kanamycin resistance, and then incubated for overnight at 37° C. 6 colonies were selected from the plate on which the transformation took place, and inoculated into 5 ml of kanamycin-containing LB for oscillating culture overnight at 37° C. Plasmids were then extracted by the plasmid extraction kit, sequenced and validated, and the successfully constructed plasmid was designated as pCDNA-C35NDC60S. The pCDNA-C35NDC60S codes parts including the 178 aa at the N-terminal of CD4 D1D2 domain, the NECK and CRD part of the DC-SIGN, and a linker containing 35 amino acids. In the pCDNA-C35NDC60S, the cysteine at position 60 of CD4 was mutated to serine.

(4) Construction of the pCDNA-C40NDC60S:

Taking pET28a-C40D (CN 102617738A) as a template, PCR was conducted with primers P1-F and P1-R, and the obtained nucleic acid amplification products were subjected to electrophoresis before gel recovery. Taking pCDNA3.1 as a template, PCR was conducted with primers P2-F and P2-R, and the obtained nucleic acid amplification products were subjected to electrophoresis before gel recovery. Homologous recombination was conducted by using a homologous recombination kit from Vazyme. 15 μl of recombination system was added to 100 μl of *Escherichia coli* competent cells DH5 alpha, mixed uniformly, the obtained mixtures were transformed by heat shock at 2° C., and then 800 μl of LB culture solution was added thereto for oscillating culture at 37° C. for 1 hour. The obtained bacteria solution was coated on an LB culture medium with kanamycin resistance, and incubated for overnight at 37° C. 6 colonies were selected from the plate on which the transformation took place, and inoculated into 5 ml of kanamycin-containing LB, for oscillating culture overnight at 37° C. Plasmids were then extracted by a plasmid extraction kit, sequenced and validated, and the successfully constructed plasmid was designated as pCDNA-C40ND.

With the properly constructed pCDNA-C40ND serving as a template and P3-F and P3-R serving as a primer pair, PCR amplification was conducted by a Takara circular PCR kit. 2 μl of dpnI was added to every 50 μl of PCR system to digest at 37° C. for 2 hours. 15 μl of obtained digestive solution was taken and added to 100 μl of *Escherichia coli* competent cells DH5 alpha, mixed uniformly, the obtained mixtures were transformed by heat shock at 42° C., and then 800 μl of LB culture solution was added thereto for oscillating culture at 37° C. for 1 hour. The obtained bacteria solution was coated on the LB culture medium with kanamycin resistance, and then incubated for overnight at 37° C. 6 colonies were selected from the plate on which the transformation took place, and inoculated into 5 ml of kanamycin-containing LB for oscillating culture overnight at 37° C. Plasmids were then extracted by the plasmid extraction kit, sequenced and validated, and the successfully constructed plasmid was designated as pCDNA-C40NDC60S. The pCDNA-C40NDC60S codes parts including the 178 aa at the N-terminal of CD4 D1D2 domain, the NECK and the CRD part of the DC-SIGN, and a linker containing 40 amino acids. In the pCDNA-C40NDC60S, the cysteine at position 60 of CD4 was mutated to serine.

(5) Construction of the pCDNA-C45NDC60S:

Taking pET28a-C45D as a template, PCR was conducted with primers P1-F and P1-R, and the obtained nucleic acid amplification products were subjected to electrophoresis before gel recovery. Taking pCDNA3.1 as a template, PCR was conducted with primers P2-F and P2-R, and the obtained nucleic acid amplification products were subjected to electrophoresis before gel recovery. Homologous recombination was conducted by using a homologous recombination kit from Vazyme. 15 μl of recombination system was added to 100 μl of *Escherichia coli* competent cells DH5 alpha, mixed uniformly, the obtained mixtures were transformed by heat shock at 42° C., and then 800 μl of LB culture solution was added thereto for oscillating culture at 37° C. for 1 hour. The obtained bacteria solution was coated on an LB culture medium with kanamycin resistance, and incubated for overnight at 37° C. 6 colonies were selected from the plate on which the transformation took place, and inoculated into 5 ml of kanamycin-containing LB for oscillating culture overnight at 37° C. Plasmids were then extracted by the plasmid extraction kit, sequenced and validated, and the successfully constructed plasmid was designated as pCDNA-C45ND.

With the properly constructed pCDNA-C45ND serving as a template and P3-F and P3-R serving as a primer pair, PCR amplification was conducted by using a Takara circular PCR kit. 2 μl of dpnI was added to every 50 μl of PCR system to digest at 37° C. for 2 hours. 15 μl of the obtained digestive solution was taken and added to 100 μl of *Escherichia coli* competent cells DH5 alpha, mixed uniformly, the mixtures were transformed by heat shock at 42° C., and then 800 μl of LB culture solution was added thereto for oscillating culture at 37° C. for 1 hour. The obtained bacteria solution was coated on the LB culture medium with kanamycin resistance, and incubated for overnight at 37° C. 6 colonies were selected from the plate on which the transformation took place, and inoculated into 5 ml of kanamycin-containing LB for oscillating culture overnight at 37° C. Plasmids were then extracted by the plasmid extraction kit, sequenced and validated, and the successfully constructed plasmid was designated as pCDNA-C45NDC60S. The pCDNA-C45NDC60S codes parts including the 178 aa at the N-terminal of CD4 D1D2 domain, the NECK and CRD of DC-SIGN, and a linker containing 45 amino acids. in the pCDNA-C45NDC60S, the cysteine at position 60 of CD4 was mutated to serine.

Example 2

Expression of the recombinant protein CLD mutant in each eukaryotic expression vector constructed in Example 1:

1. Cell Culture

Cells were cultured to passage at a density of 600000 to 700000 cells/ml, and the total volume was 30 ml. When the density of 293F cells reached to 1.2-1.5 million cells/ml, the cells were collected (by configuring at 1200 rpm for 5 minutes), and resuspended in 15 ml of culture medium for transfection.

2. Transfection

For the transfection of every one million cells, 1 μg to 1.5 μg of plasmids were used. 750 μl of physiological saline+37.5 μg of plasmids, and 750 μl of physiological saline+150 μl of PEI (1 mg/ml) were allowed to stand for 5 minutes after being mixed uniformly respectively, and then mixed them gently and uniformly, and the obtained mixture was allowed to stand at room temperature for 10 minutes (but less than 20 minutes). Then the obtained mixture of plasmid-lipidosome was added to a shake flask, and put into a shaker (8% $CO_2$, 37° C., 125 rpm) after being mixed uniformly. 4 hours to 6 hours later, 15 ml of culture medium was supplemented. Cell supernatants were collected after 4 days, ultrafiltered and concentrated with a 50 KD ultrafiltration tube, and finally concentrated by about 80 times. 10% glycerol was added to the obtained concentrate before subpackaging and storing at −80° C. for later use.

In the present application, the protein expressed by the eukaryotic expression plasmid pCDNA-C25NDC60S was called C25NDC60S (as shown in SEQ ID NO. 1), the protein expressed by the pCDNA-C30NDC60S was called C30NDC60S (as shown in SEQ ID NO. 2), the protein expressed by the pCDNA-C35NDC60S was called C35NDC60S (as shown in SEQ ID NO. 3), the protein expressed by the pCDNA-C40NDC60S was called C40NDC60S (as shown in SEQ ID NO. 4), and the protein expressed by the pCDNA-C45NDC60S was called C45NDC60S (as shown in SEQ ID NO. 5).

3. Concentration Detection of the Recombinant Protein CLD Mutant in ELISA (1) A 96-well plate was coated with rabbit-derived anti-DC-SIGN monoclonal antibodies at 5 μg/ml (50 μl/well), and placed for overnight at room temperature;

The 96-well plate was eluted by a micro-plate washer for 5 times, then 200 μl PBS blocking buffer containing 1% BSA was added to each well, and blocked at 37° C. for one hour.

(2) The 96-well plate was eluted by the micro-plate washer for 5 times, a standard sample (prokaryotically expressed CLD)/recombinant protein sample was incubated at 50 μl/well. The incubation was conducted at 37° C. for one hour, and the standard sample was diluted with the blocking buffer;

(3) The 96-well plate was eluted by the micro-plate washer for 5 times, anti-CLD serum derived from an immunized mouse (diluted with the blocking buffer according to the ratio of 1:1000) was added thereto (50 μl/well), and then incubation was conducted at 37° C. for one hour;

(4) The 96-well plate was eluted by the micro-plate washer for 5 times, second antibodies of goat anti-mouse IgG labeled by HRP (diluted with the blocking buffer according to the ratio of 1:10000) were added thereto (50 μl/well), and then incubation was conducted at 37° C. for one hour;

(5) The 96-well plate was eluted by the micro-plate washer for 5 times, a TMB substrate placed at room temperature in advance was added thereto at 50 μl/well, and incubation was conducted in the dark at room temperature for 5 minutes;

(6) Termination of the reaction: a 2 M $H_2SO_4$ solution was added at 50 μl/well, and reading was conducted by an ELISA analyzer; and (7) A standard curve was drawn, and the concentration of the recombinant protein CLD mutant was calculated.

The concentration of the recombinant protein CLD mutant prepared by the above method is 100 μg/ml.

Example 3

Application of the CLD recombinant protein and recombinant protein CLD mutant in the manufacture of drugs for the treatment or prevention of HIV-1 virus:

1) Preparation of HIV-1 pseudovirus:

293T cells were co-transfected with pCDNA3.1 (+) plasmids (Centralized Facility for AIDS Reagents) containing different HIV-1env genes and HIV-1env gene deleted pSG3 (Centralized Facility for AIDS Reagents) framework plasmids via lipidosome (Lipofectamine™ 2000, Invitrogen Corporation). After the transfection was conducted for 48 hours, supernatants of the culture medium containing viruses were filtered by a 0.45 μm filter membrane, and then 10% volume of fetal calf serum was added thereto, the obtained products were subpackaged in 1.5 ml centrifuge tubes, and stored at −80° C. for later use. Viral titer was determined with luciferase (commercially available, Promega).

The different HIV-1env genes contained in the above different pCDNA3.1 (+) plasmids are: MSW2, CH811, 700010040.C9.4520, PRB958_06.TB1.4305, WEAUd15.410.787, 62357_14.D3.4589, REJO.D12.1972, SC05.8C11.2344, 1059_09.A4.1460, 6240_08.TA5.4622, 700010058.A4.4375, 1058_11.B11.1550, SC45.4B5.2631, and 62615_03.P4.3964.

2) Preparation of HIV-1 euvirus:

293T cells were transfected by different plasmids containing HIV-1 whole genome via lipidosome (Lipofectamine™ 2000, Invitrogen Corporation). After the transfection was conducted for 48 hours, supernatants of the culture medium containing the viruses were filtered by the 0.45 μm filter membrane, and then 10% volume of fetal calf serum was added thereto, the obtained products were subpackaged in 1.5 ml centrifuge tubes, and stored at −80° C. for later use. Viral titer was determined by using luciferase (commercially available, Promega).

The above different plasmids are laboratory-adapted strains NL4-3 and BaL; T/F strains include THRO.c/2626, CH077.t/2627, CH040.c/2625, pCH058.c/2960, WITO.c/2474, SUMA.c/2821, CH164, CH185 and CH198.

3) Inhibition of recombinant proteins to HIV-1 from infecting TZM-b1 cell line:

A). All recombinant protein solutions were diluted to 1 μM (as an initial concentration), at which the solutions were diluted by 11 gradients downwards by taking 3 as a dilution coefficient, and finally a culture medium without the recombinant proteins was set as a control;

B). The viruses were diluted to 200TCID50;

C). 60 μl of properly diluted viruses were mixed with 60 μl of diluents of the recombinant proteins, and the mixtures were incubated at 37° C. for 1 hour;

D). 100 μl of the mixtures of the virus-recombinant protein was added to TZM-b1 cells which had been spread in the 96-well plate in advance, then 100 μl of complete culture medium containing DEAE (40 μg/ml) was added thereto, and the cells were cultured in a carbon dioxide incubator for 48 hours;

E). A fluorescence value was determined by using the luciferase plate reader (commercially available, Promega);

F). An inhibition ratio was calculated, and the reading of the well without CLD was considered as 0% inhibition ratio.

Results are shown in the following table, in which:

C25ND and C35ND are prokaryotically expressed CLD recombinant proteins disclosed in CN 102617738A:

The C35NDS60C protein is derived from "*Bifunctional CD4-DC-SIGN Fusion Proteins Demonstrate Enhanced Avidity to gp*120 *and Inhibit HIV-*1 *Infection and Dissemination*".

| strain | subtype | C25 ND | C35 ND | C35N DS60C | C25N DC60S | C30N DC60S | C35N DC60S | C40N DC60S | C45N DC60S |
|---|---|---|---|---|---|---|---|---|---|
| BaL | B | 4.9 | 5.3 | 3.3 | 13.52 | 2.15 | 1.14 | 0.34 | 0.62 |
| NL4-3 | B | | | | 12.14 | 1.23 | 0.61 | 0.20 | 0.37 |
| THRO.c/2626 | B | | | | 22.80 | 1.84 | 0.68 | 0.29 | 0.52 |
| CH040.c/2625 | B | | | | 82.07 | 12.04 | 2.41 | 1.01 | 1.81 |
| CH077.t/2627 | B | | | | 53.14 | 5.48 | 2.83 | 0.91 | 1.64 |
| CH058.c/2960 | B | | | | 10.05 | 8.03 | 2.31 | 1.01 | 1.81 |
| WITO.c/2474 | B | | | | 785.13 | 13.48 | 4.43 | 2.41 | 4.34 |
| SUMA.c/2821 | B | | | | >1000 | 598.23 | 10.74 | 4.37 | 7.87 |
| 62357_14.D3.4589 | C | | | | 13.08 | 7.85 | 2.62 | 1.31 | 2.35 |
| REJO.D12.1972 | C | | | | >1000 | 514.75 | 30.92 | 1.96 | 3.52 |
| 700010040.C9.4520 | C | | | | 420.10 | 15.06 | 8.02 | 2.01 | 3.62 |
| PRB958_6.TB1.4305 | C | | | | 4.74 | 2.84 | 2.95 | 0.47 | 1.85 |
| WEAUd15.410.787 | C | | | | >1000 | 6.55 | 3.85 | 0.92 | 1.66 |
| SC05.8C11.2344 | C | | | | >1000 | 20.53 | 11.51 | 3.76 | 9.76 |
| 1059_09.A4.1460 | C | | | | 562.75 | 25.65 | 8.55 | 2.28 | 6.10 |
| 6240_08.TA5.4622 | C | | | | 64.75 | 6.85 | 3.95 | 0.98 | 2.76 |
| 700010058.A4.4375 | C | | | | 14.69 | 4.82 | 2.94 | 0.47 | 1.84 |
| 1058_11.B11.1550 | C | | | | 23.19 | 6.91 | 1.64 | 0.32 | 1.37 |
| SC45.4B5.2631 | C | | | | 79.88 | 4.93 | 1.98 | 0.99 | 1.78 |
| 62615_03.P4.3964 | C | | | | 20.27 | 15.16 | 6.05 | 2.03 | 4.65 |
| CH164 | C | | | | >1000 | 52.81 | 21.94 | 5.97 | 6.74 |
| CH198 | C | | | | 23.39 | 4.03 | 2.68 | 0.34 | 0.81 |
| CH185 | C | | | | 130.88 | 12.33 | 4.78 | 1.39 | 3.50 |
| CH811 | C | 56.7 | 42.8 | 4.7 | 47.24 | 78.34 | 11.45 | 4.72 | 6.50 |
| MSW2 | | 578.6 | 667.3 | 13 | 104.50 | 8.30 | 4.10 | 1.05 | 6.89 |

The blank in the table represents no such data.

The results show that the CLD protein mutant has better inhibiting effects on various HIV-1 viruses than that of the prokaryotically expressed CLD recombinant proteins disclosed in CN 102617738A.

Example 4

Application of the complex immunogen prepared from any one of the 8 recombinant proteins CLD in CN 102617738A and HIV-1 envelope protein in the manufacture of drugs for the prevention of HIV-1:

1) Preparation of the complex immunogens of the recombinant protein CLD and the HIV-1 envelope protein, CD4 and the HIV-1 envelope protein, and DC-SIGN and the HIV-1 envelope protein:

Experimental group: the recombinant protein CLD and the HIV-1 envelope protein (5 μg) were mixed according to a molar ratio of 3:1, and the obtained mixtures were incubated at 4° C. for 24 hours, totaling 100 μl;

The recombinant protein CLD described above was any one of proteins of claims 1-8 in CN 102617738A.

Control group 1: the CD4 and the HIV-1 envelope protein (5 μg) were mixed according to a molar ratio of 12:1, and the obtained mixtures were incubated at 4° C. for 24 hours, totaling 100 μl;

Control group 2: the DC-SIGN and the HIV-1 envelope protein (5 μg) were mixed according to a molar ratio of 3:1, and the obtained mixtures were incubated at 4° C. for 24 hours, totaling 100 μl; and The recombinant protein CLD and DC-SIGN appear in a tetramer form, one CLD tetramer contains four CD4 and one DC-SIGN, and therefore the molar ratio used in the control group 1 and control group 2 is 12:1 and 3:1, respectively.

The HIV-1 envelope protein is gp140 protein of HIV-1 CN54.

2) Immunization of mice: 100 μl of reagents of each group prepared in step 1) was administrated by subcutaneous injection to immunize the mice, the immunization was conducted for 3 times in total, and the interval between every two immunizations was 3 weeks. On Day 7 after the last immunization, the mice were sacrificed and the serum and spleen of them were collected;

3) Experimental method

A). In order to investigate whether the binding of the CD4 to gp140 can affect its conformation and expose a CD4i epitope or not, 6 monoclonal antibodies of 17b (CD4i), 19b (CD4i), 447-52D (V3), 39F (V3), 12b (CD4BS) and F105 which identify different gp120 target sites were selected in this experiment to perform ELISA experiments. A 96-well plate was coated with gp140 or mixtures of the gp140 and the recombinant protein CLD (0.25 μg/well), placed overnight at room temperature, washed with TBST for three times, and then blocked with TBST containing 1% BSA at 37° C. for 1 hour. The above antibodies diluted serially were added and the plate was then incubated at 37° C. for 1 hour. HRP-labeled goat anti-mouse second antibodies (diluted at a ratio of 1:5000) were added for incubation at 37° C. for 1 hour after washing the plate for three times with TBST. After 5 times washing, TMB was added, the incubation was conducted in the dark at room temperature for 5 minutes, and then 2 M concentrated sulfuric acid was added for terminating the reaction. Finally, an OD value was determined by an ELISA analyzer, in which 450 nm served as an experiment wavelength and 570 nm served as a reference wavelength.

B). In order to investigate a titer of gp140 specific antibodies tested in serum in ELISA, the 96-well plate was coated with gp140 or mixtures of the gp140 and sCD4 (0.25 μg/well), placed overnight at room temperature, washed with TBST for three times, and then blocked with TBST containing 1% BSA at 37° C. for 1 hour. The samples diluted serially were added and the plate was then incubated at 37° C. for 1 hour. After the plate was washed for three times with TBST, the HRP-labeled goat anti-mouse second antibodies (diluted at a ratio of 1:5000) were added for incubation at 37° C. for 1 hour. After 5 times washing, the TMB was added, the incubation was conducted in the dark at room temperature for 5 minutes, and then 2 M concentrated sulfuric acid was added for terminating the reaction. Finally, an OD value was determined by the ELISA analyzer, in which 450 nm served as the experiment wavelength and 570 nm served as the reference wavelength.

C). Cytokine detection

The spleen of the mouse in the experimental group was taken, and lymphocytes were separated therefrom. $3\times10^7$ cells were spread in each well of a 24-well plate, stimulated with gp140 (20 μg/well) or CLD-gp140 (35 μg/well), and the supernatants were collected after 5 days, filtered by a 0.22 um filter, the obtained products were subpackaged and stored at −80° C. for later use. The amounts of IL-2, IL-4, IL-5, IFN-gamma and TNF-alpha were detected by a BD Biosciences cytokine kit.

4) Experimental results

The recombinant protein CLD in CN 102617738A affect the binding of mAbs (17b, 19b, 447-52D, 39F, b12 and F105) to the HIV-1 gp140.

Compared with the complex of CD4 and the HIV-1 envelope protein, or the complex of DC-SIGN and the HIV-1 envelope protein, or a single envelope protein, the complex consisting of the recombinant protein CLD in CN 102617738A and the HIV-1 envelope protein could induce an organism to produce more vigorous antibody responses targeting gp120 V1V2 epitopes as an immunogen, but the resulted antibody responses targeting gp120 V3C3 epitopes are weaker.

Compared with the complex of CD4 and the HIV-1 envelope protein, or the complex of DC-SIGN and the HIV-1 envelope protein, or a single envelope protein, the complex consisting of the recombinant protein CLD in CN 102617738A and the HIV-1 envelope protein could induce the organism to produce different gp140-specific Th1/Th2 cellular immune responses as the immunogen. In the spleen cells of the mouse which is immunized by the complex consisting of a CLD mutant and the HIV-1 envelope protein, gp140-specific cells with expressions to IL-4, IL-5 and IFN-gamma are reduced significantly; and cells with the expression to TNF are also reduced, but there is no significant difference.

Example 5

Application of the complex immunogen of the CLD protein mutant and the HIV-1 envelope protein in the prevention of HIV-1 viruses:

1) Preparation of the complex immunogens of the CLD protein mutant and the HIV-1 envelope protein, CD4 and the HIV-1 envelope protein, and DC-SIGN and the HIV-1 envelope protein:

Experimental group: the CLD protein mutant and the HIV-1 envelope protein (5 μg) were mixed according to a ratio (molar ratio) of 3:1, and the obtained mixtures were incubated at 4° C. for 24 hours, totaling 100 μl;

The CLD protein mutant described above was a protein as shown in SEQ ID NO. 1, SEQ ID NO. 2, SEQ ID NO. 3, SEQ ID NO. 4 or SEQ ID NO. 5.

Control group 1: the CD4 and the HIV-1 envelope protein (5 μg) were mixed according to a ratio (molar ratio) of 12:1, and the obtained mixtures were incubated at 4° C. for 24 hours, totaling 100 μl;

Control group 2: the DC-SIGN and the HIV-1 envelope protein (5 μg) were mixed according to a ratio (molar ratio) of 3:1, and the obtained mixtures were incubated at 4° C. for 24 hours, totaling 100 μl; and The recombinant protein CLD and DC-SIGN appear in a tetramer form, one CLD tetramer contains four CD4 and one DC-SIGN, and therefore the molar ratio used in the control group 1 and control group 2 is 12:1 and 3:1, respectively.

The HIV-1 envelope protein is gp140 protein of HIV-1 CN54.

2) Immunization of mice: 100 μl of reagents of each group prepared in step 1) was administrated by subcutaneous injection to immunize the mice, the immunization was conducted for 3 times in total, and the interval between every two immunizations was 3 weeks. On Day 7 after the last immunization, the mice were sacrificed and the serum and spleen of them were collected;

3) Experimental method

A). In order to investigate whether the binding of the CD4 to gp140 can affect its conformation and expose a CD4i epitope or not, 6 monoclonal antibodies of 17b (CD4i), 19b (CD4i), 447-52D (V3), 39F (V3), 12b (CD4BS) and F105 which identify different gp120 target sites were selected in this experiment to perform ELISA experiments. A 96-well plate was coated with gp140 or mixtures of the gp140 and the recombinant protein CLD (0.25 μg/well), placed overnight at room temperature, washed with TBST for three times, and then blocked with TBST containing 1% BSA at 37° C. for 1 hour. The above antibodies diluted serially were added and the plate was then incubated at 37° C. for 1 hour. HRP-labeled goat anti-mouse second antibodies (diluted at a ratio of 1:5000) were added for incubation at 37° C. for 1 hour after washing the plate for three times with TB ST. After 5 times washing, TMB was added, the incubation was conducted in the dark at room temperature for 5 minutes, and then 2 M concentrated sulfuric acid was added for terminating the reaction. Finally, an OD value was determined by the ELISA analyzer, in which 450 nm served as the experiment wavelength and 570 nm served as the reference wavelength.

B). In order to investigate a titer of gp140 specific antibodies tested in serum in ELISA, the 96-well plate was coated with gp140 or mixtures of the gp140 and sCD4 (0.25 μg/well), placed overnight at room temperature, washed with TBST for three times, and then blocked with TBST containing 1% BSA at 37° C. for 1 hour. The samples diluted serially were added and the plate was then incubated at 37° C. for 1 hour. After the plate was washed with TBST for three times, the HRP-labeled goat anti-mouse second antibodies (diluted at a ratio of 1:5000) were added for incubation at 37° C. for 1 hour. After 5 times washing, the TMB was added, the incubation was conducted in the dark at room temperature for 5 minutes, and then 2 M concentrated sulfuric acid was added for terminating the reaction. Finally, an OD value was determined by the ELISA analyzer, in which 450 nm served as the experiment wavelength and 570 nm served as the reference wavelength.

C). Cytokine detection

The spleen of the mouse in the experimental group was taken, and lymphocytes were separated therefrom. $3\times10^7$ cells were spread in each well of a 24-well plate, stimulated with gp140 (20 μg/well) or CLD-gp140 (35 μg/well), and the supernatants were collected after 5 days, filtered by a 0.22 um filter, the obtained products were subpackaged and stored at −80° C. for later use. The amounts of IL-2, IL-4, IL-5, IFN-gamma and TNF-alpha were detected by a BD Biosciences cytokine kit.

4) Experimental results

Compared with the recombinant protein CLD used in Example 4, the CLD mutant of the present application has a higher effect on the binding of mAbs (17b, 19b, 447-52D, 39F, b12 and F105) to the HIV-1 gp140.

Compared with the complex of CD4 and the HIV-1 envelope protein, or the complex of DC-SIGN and the HIV-1 envelope protein, or the single envelope protein, the complex consisting of the CLD protein mutant and the HIV-1 envelope protein in the present application could induce the organism to produce the more vigorous antibody responses targeting gp120 V1V2 epitopes as the immunogen, but the resulted antibody responses targeting gp120 V3C3 epitopes are weaker. Compared with the recombinant protein CLD in Example 4, the produced difference is more obvious.

Compared with the complex of CD4 and the HIV-1 envelope protein, or the DC-SIGN and the HIV-1 envelope protein, or the single envelope protein, the complex consisting of the CLD mutant and the HIV-1 envelope protein in the present application could induce the organism to produce different gp140-specific Th1/Th2 cellular immune responses as the immunogen. In the spleen cells of the mouse which is immunized by the complex consisting of the CLD mutant and the HIV-1 envelope protein, gp140-specific cells with expressions to IL-4, IL-5, TNF and IFN-gamma are reduced significantly. Compared with the recombinant protein CLD in Example 4, the produced difference is more obvious.

What is claimed is:

1. A CLD protein mutant, wherein the CLD protein mutant is shown in SEQ ID NO. 4.

2. A method of using the CLD protein mutant of claim 1 for treating HIV-1, comprising: administering a therapeutic effective amount of the CLD protein mutant to a subject in need.

3. A composition of CLD protein mutants, wherein the composition is a combination of SEQ ID NO. 4 and any one, two, three or four of proteins as shown in SEQ ID NOs.1, 2, 3, and 5.

4. A method of using the composition of claim 3 for treating HIV-1, comprising: administering a therapeutic effective amount of the composition to a subject in need.

5. A complex immunogen comprising any one of proteins as shown in the SEQ ID NO. 1 to SEQ ID NO. 5, and HIV-1 gp160, HIV-1 gp140 or HIV-1 gp120.

6. A method of using the complex immunogen of claim 5 for treating HIV-1, comprising: administering a therapeutic effective amount of the complex immunogen to a subject in need.

7. A complex immunogen consisting of a recombinant CLD protein and a HIV-1 envelope protein, wherein the recombinant CLD protein is any one of proteins as shown in the SEQ ID NO. 6 to SEQ ID NO. 8.

8. A method of using the complex immunogen of claim 7 for treating HIV-1, comprising: administering a therapeutic effective amount of the complex immunogen to a subject in need.

* * * * *

SEQUENCE LISTING

```
Sequence total quantity: 8
SEQ ID NO: 1            moltype = AA  length = 541
FEATURE                 Location/Qualifiers
source                  1..541
                        mol_type = protein
                        organism = synthetic construct
SEQUENCE: 1
MDRAKLLLLL LLLLLPQAQA VKKVVLGKKG DTVELTCTAS QKKSIQFHWK NSNQIKILGN  60
QGSFLTKGPS KLNDRADSRR SLWDQGNFPL IIKNLKIEDS DTYICEVEDQ KEEVQLLVFG  120
LTANSDTHLL QGQSLTLTLE SPPGSSPSVQ CRSPRGKNIQ GEKTLSVSQL ELQDSGTWTC  180
TVLQNQKKVE FKIDIVVLAG GGGSGGGGSG GGGSGGGGSG GGGSVGELSE KSKLQEIYQE  240
LTQLKAAVGE LPEKSKLQEI YQELTRLKAA VGELPEKSKL QEIYQELTWL KAAVGELPEK  300
SKMQEIYQEL TRLKAAVGEL PEKSKQQEIY QELTRLKAAV GELPEKSKQQ EIYQELTRLK  360
AAVGELPEKS KQQEIYQELT QLKAAVERLC HPCPWEWTFF QGNCYFMSNS QRNWHDSITA  420
CKEVGAQLVV IKSAEEQNFL QLQSSRSNRF TWMGLSDLNQ EGTWQWVDGS PLLPSFKQYW  480
NRGEPNNVGE EDCAEFSGNG WNDDKCNLAK FWICKKSAAS CSRDEEQFLS PAPATPNPPP  540
A                                                                 541

SEQ ID NO: 2            moltype = AA  length = 546
FEATURE                 Location/Qualifiers
source                  1..546
                        mol_type = protein
                        organism = synthetic construct
SEQUENCE: 2
```

-continued

```
MDRAKLLLLL LLLLLPQAQA VKKVVLGKKG DTVELTCTAS QKKSIQFHWK NSNQIKILGN  60
QGSFLTKGPS KLNDRADSRR SLWDQGNFPL IIKNLKIEDS DTYICEVEDQ KEEVQLLVFG  120
LTANSDTHLL QGQSLTLTLE SPPGSSPSVQ CRSPRGKNIQ GEKTLSVSQL ELQDSGTWTC  180
TVLQNQKKVE FKIDIVVLAG GGGSGGGGSG GGGSGGGGSG GGGSGGGGSV GELSEKSKLQ  240
EIYQELTQLK AAVGELPEKS KLQEIYQELT RLKAAVGELP EKSKLQEIYQ ELTWLKAAVG  300
ELPEKSKMQE IYQELTRLKA AVGELPEKSK QQEIYQELTR LKAAVGELPE KSKQQEIYQE  360
LTRLKAAVGE LPEKSKQQEI YQELTQLKAA VERLCHPCPW EWTFFQGNCY FMSNSQRNWH  420
DSITACKEVG AQLVVIKSAE EQNFLQLQSS RSNRFTWMGL SDLNQEGTWQ WVDGSPLLPS  480
FKQYWNRGEP NNVGEEDCAE FSGNGWNDDK CNLAKFWICK KSAASCSRDE EQFLSPAPAT  540
PNPPPA                                                            546

SEQ ID NO: 3           moltype = AA  length = 551
FEATURE                Location/Qualifiers
source                 1..551
                       mol_type = protein
                       organism = synthetic construct
SEQUENCE: 3
MDRAKLLLLL LLLLLPQAQA VKKVVLGKKG DTVELTCTAS QKKSIQFHWK NSNQIKILGN  60
QGSFLTKGPS KLNDRADSRR SLWDQGNFPL IIKNLKIEDS DTYICEVEDQ KEEVQLLVFG  120
LTANSDTHLL QGQSLTLTLE SPPGSSPSVQ CRSPRGKNIQ GEKTLSVSQL ELQDSGTWTC  180
TVLQNQKKVE FKIDIVVLAG GGGSGGGGSG GGGSGGGGSG GGGSGGGGSG GGGSVGELSE  240
KSKLQEIYQE LTQLKAAVGE LPEKSKLQEI YQELTRLKAA VGELPEKSKL QEIYQELTWL  300
KAAVGELPEK SKMQEIYQEL TRLKAAVGEL PEKSKQQEIY QELTRLKAAV GELPEKSKQQ  360
EIYQELTRLK AAVGELPEKS KQQEIYQELT QLKAAVERLC HPCPWEWTFF QGNCYFMSNS  420
QRNWHDSITA CKEVGAQLVV IKSAEEQNFL QLQSSRSNRF TWMGLSDLNQ EGTWQWVDGS  480
PLLPSFKQYW NRGEPNNVGE EDCAEFSGNG WNDDKCNLAK FWICKKSAAS CSRDEEQFLS  540
PAPATPNPPP A                                                      551

SEQ ID NO: 4           moltype = AA  length = 556
FEATURE                Location/Qualifiers
source                 1..556
                       mol_type = protein
                       organism = synthetic construct
SEQUENCE: 4
MDRAKLLLLL LLLLLPQAQA VKKVVLGKKG DTVELTCTAS QKKSIQFHWK NSNQIKILGN  60
QGSFLTKGPS KLNDRADSRR SLWDQGNFPL IIKNLKIEDS DTYICEVEDQ KEEVQLLVFG  120
LTANSDTHLL QGQSLTLTLE SPPGSSPSVQ CRSPRGKNIQ GEKTLSVSQL ELQDSGTWTC  180
TVLQNQKKVE FKIDIVVLAG GGGSGGGGSG GGGSGGGGSG GGGSGGGGSG GGGSGGGGSV  240
GELSEKSKLQ EIYQELTQLK AAVGELPEKS KLQEIYQELT RLKAAVGELP EKSKLQEIYQ  300
ELTWLKAAVG ELPEKSKMQE IYQELTRLKA AVGELPEKSK QQEIYQELTR LKAAVGELPE  360
KSKQQEIYQE LTRLKAAVGE LPEKSKQQEI YQELTQLKAA VERLCHPCPW EWTFFQGNCY  420
FMSNSQRNWH DSITACKEVG AQLVVIKSAE EQNFLQLQSS RSNRFTWMGL SDLNQEGTWQ  480
WVDGSPLLPS FKQYWNRGEP NNVGEEDCAE FSGNGWNDDK CNLAKFWICK KSAASCSRDE  540
EQFLSPAPAT PNPPPA                                                 556

SEQ ID NO: 5           moltype = AA  length = 561
FEATURE                Location/Qualifiers
source                 1..561
                       mol_type = protein
                       organism = synthetic construct
SEQUENCE: 5
MDRAKLLLLL LLLLLPQAQA VKKVVLGKKG DTVELTCTAS QKKSIQFHWK NSNQIKILGN  60
QGSFLTKGPS KLNDRADSRR SLWDQGNFPL IIKNLKIEDS DTYICEVEDQ KEEVQLLVFG  120
LTANSDTHLL QGQSLTLTLE SPPGSSPSVQ CRSPRGKNIQ GEKTLSVSQL ELQDSGTWTC  180
TVLQNQKKVE FKIDIVVLAG GGGSGGGGSG GGGSGGGGSG GGGSGGGGSG GGGSGGGGSG  240
GGGSVGELSE KSKLQEIYQE LTQLKAAVGE LPEKSKLQEI YQELTRLKAA VGELPEKSKL  300
QEIYQELTWL KAAVGELPEK SKMQEIYQEL TRLKAAVGEL PEKSKQQEIY QELTRLKAAV  360
GELPEKSKQQ EIYQELTRLK AAVGELPEKS KQQEIYQELT QLKAAVERLC HPCPWEWTFF  420
QGNCYFMSNS QRNWHDSITA CKEVGAQLVV IKSAEEQNFL QLQSSRSNRF TWMGLSDLNQ  480
EGTWQWVDGS PLLPSFKQYW NRGEPNNVGE EDCAEFSGNG WNDDKCNLAK FWICKKSAAS  540
CSRDEEQFLS PAPATPNPPP A                                           561

SEQ ID NO: 6           moltype = AA  length = 294
FEATURE                Location/Qualifiers
source                 1..294
                       mol_type = protein
                       organism = synthetic construct
SEQUENCE: 6
MGSSHHHHHH SSGLVPRGSH MKKVVLGKKG DTVELTCTAS QKKSIQFHWK NSNQIKILGN  60
QGSFLTKGPS KLNDRADSRR SLWDQGNFPL IIKNLKIEDS DTYICEVEGG GGSGGGGSGG  120
GGSGGGGSGG GGSGGGGSGG GGSHPCPWEW TFFQGNCYFM SNSQRNWHDS ITACKEVGAQ  180
LVVIKSAEEQ NFLQLQSSRS NRFTWMGLSD LNQEGTWQWV DGSPLLPSFK QYWNRGEPNN  240
VGEEDCAEFS GNGWNDDKCN LAKFWICKKS AASCSRDEEQ FLSPAPVTPN PPPA       294

SEQ ID NO: 7           moltype = AA  length = 541
FEATURE                Location/Qualifiers
source                 1..541
                       mol_type = protein
                       organism = synthetic construct
```

-continued

```
SEQUENCE: 7
MGSSHHHHHH SSGLVPRGSH MKKVVLGKKG DTVELTCTAS QKKSIQFHWK NSNQIKILGN  60
QGSFLTKGPS KLNDRADSRR SLWDQGNFPL IIKNLKIEDS DTYICEVEDQ KEEVQLLVFG  120
LTANSDTHLL QGQSLTLTLE SPPGSSPSVQ CRSPRGKNIQ GEKTLSVSQL ELQDSGTWTC  180
TVLQNQKKVE FKIDIVVLAG GGGSGGGGSG GGGSGGGGSG GGGSVGELSE KSKLQEIYQE  240
LTQLKAAVGE LPEKSKLQEI YQELTRLKAA VGELPEKSKL QEIYQELTWL KAAVGELPEK  300
SKMQEIYQEL TRLKAAVGEL PEKSKQQEIY QELTRLKAAV GELPEKSKQQ EIYQELTRLK  360
AAVGELPEKS KQQEIYQELT QLKAAVERLC HPCPWEWTFF QGNCYFMSNS QRNWHDSITA  420
CKEVGAQLVV IKSAEEQNFL QLQSSRSNRF TWMGLSDLNQ EGTWQWVDGS PLLPSFKQYW  480
NRGEPNNVGE EDCAEFSGNG WNDDKCNLAK FWICKKSAAS CSRDEEQFLS PAPATPNPPP  540
A                                                                541

SEQ ID NO: 8            moltype = AA  length = 551
FEATURE                 Location/Qualifiers
source                  1..551
                        mol_type = protein
                        organism = synthetic construct
SEQUENCE: 8
MGSSHHHHHH SSGLVPRGSH MKKVVLGKKG DTVELTCTAS QKKSIQFHWK NSNQIKILGN  60
QGSFLTKGPS KLNDRADSRR SLWDQGNFPL IIKNLKIEDS DTYICEVEDQ KEEVQLLVFG  120
LTANSDTHLL QGQSLTLTLE SPPGSSPSVQ CRSPRGKNIQ GEKTLSVSQL ELQDSGTWTC  180
TVLQNQKKVE FKIDIVVLAG GGGSGGGGSG GGGSGGGGSG GGGSGGGGSG GGGSVGELSE  240
KSKLQEIYQE LTQLKAAVGE LPEKSKLQEI YQELTRLKAA VGELPEKSKL QEIYQELTWL  300
KAAVGELPEK SKMQEIYQEL TRLKAAVGEL PEKSKQQEIY QELTRLKAAV GELPEKSKQQ  360
EIYQELTRLK AAVGELPEKS KQQEIYQELT QLKAAVERLC HPCPWEWTFF QGNCYFMSNS  420
QRNWHDSITA CKEVGAQLVV IKSAEEQNFL QLQSSRSNRF TWMGLSDLNQ EGTWQWVDGS  480
PLLPSFKQYW NRGEPNNVGE EDCAEFSGNG WNDDKCNLAK FWICKKSAAS CSRDEEQFLS  540
PAPATPNPPP A                                                     551
```